US00PP11902P2

(12) United States Plant Patent
Werner et al.

(10) Patent No.: US PP11,902 P2
(45) Date of Patent: Jun. 5, 2001

(54) PEACH TREE NAMED 'CORINTHIAN PINK'

(76) Inventors: Dennis James Werner, 268 Kilgore Hall Horticultural Science Department North Carolina State University; Steve Martin Worthington; Layne Karlton Snelling, both of 59 Kilgore Hall Horticultural Science Department North Carolina State University, all of Raleigh, NC (US) 27695-7609

( * ) Notice: Subject to any disclaimer, the term of this patent is extended or adjusted under 35 U.S.C. 154(b) by 0 days.

(21) Appl. No.: 09/143,339

(22) Filed: Aug. 28, 1998

(51) Int. Cl.[7] ..... A01H 5/00
(52) U.S. Cl. ..... Plt./196
(58) Field of Search ..... Plt./194, 187, 199, Plt./191, 180, 196

*Primary Examiner*—Bruce R. Campell
*Assistant Examiner*—Wendy A Baker

(57) ABSTRACT

A new and distinct cultivar of ornamental peach tree called 'Corinthian Pink' is provided that demonstrates a norrowly columnar growth habit, a vigorous growth rate, medium purple foliage, and an abundance of light pink-colored, double flowers. The new cultivar produces very few fruit, and is intended for use as a spring flowering ornamental plant in the home landscape.

6 Drawing Sheets

SUMMARY OF THE INVENTION

The new and distinct variety of peach (*Prunus persica* (L.) Batsch) originated as a second generation descendant from a hand pollinated cross of North Carolina Selection 'NC174RL' nectarine (non-patented)×a selection of Japanese 'Pillar' peach made in 1983 at the Sandhills Research Station at Jackson Springs, N.C. The parent plants used in this hybridization have not been named and released and are unavailable in commerce.

The seeds resulting from this controlled hybridization were germinated in a greenhouse at North Carolina State University, Raleigh, N.C. in the Fall of 1983 and planted in the field in Spring of 1984. These trees were grown to maturity; trees were self pollinated in Spring of 1988, and the resultant seed was harvested in August 1988. This seed was sown directly in the field in November 1988, and seedlings flowered in 1991. One seedling, designated NC174RLxPil-172, was selected for its medium purple foliage color, narrowly columnar growth habit, and heavy production of light pink, double flowers.

During 1993 and 1996, the original plant selection was propagated asexually by grafting of vegetative buds onto peach seedling rootstock, cultivar 'Lovell', at the Sandhills Research Station. A grafted tree of the variety was established at the North Carolina State University Lake Wheeler Field Laboratory Research Station in Raleigh, N.C. Subsequently, a larger test planting has been established with asexually multiplied plants at the Sandhills Research Station, at the above noted location.

The new variety has routinely been asexually multiplied by grafting, specifically 'T' and chip budding. It readily forms a graft union with 'Lovell' peach rootstock and resumes normal growth. During all asexual propagation, the characteristics of the original plant have been maintained and no aberrant phenotypes have appeared.

Test plantings at the two research station locations noted above, which vary considerably in soil and climatic conditions, demonstrate this variety to be widely adapted to differing soil and climatic conditions.

Plants and fruit of this new variety differ phenotypically from its antecedents. The new variety produces medium purple leaves and light pink double flowers, differing from the single pink flowers of 'NC174RL' and the double pink and white variegated flowers, and green leaves of the Japanese 'Pillar' peach antecedent. Growth habit is narrowly columnar, and fruit are pubescent (peach), distinguishing it from the 'NC174RL' nectarine antecedent. Plants of 'Corinthian Pink' differ from 'Corinthian Rose', U.S. Plant Pat. No. 11,564, in having lighter pink flower color and lighter purple foliage. Fruit of this new variety are small and of poor quality, and are of no commercial importance.

Plants of the new variety are very vigorous and grow rapidly after establishment of trees in the field. Young trees have average 3–4 feet of growth per year. A four-year-old tree measured in Raleigh, N.C. was 14.0 feet in height and 4.5 feet in spread, with spread measured 6 feet from ground level. Trunk diameter (girth) was 3.9 inches, measured one foot from ground level. Plants are narrowly columnar in growth habit. The branch angles between the trunk and lateral branches of 'Corinthian Pink' measure between 5 to 20 degrees, in comparison to non-columnar peach varieties such as 'Contender' (unpatented), which typically measure between 35 to 50 degrees.

Flowering sometimes occurs in the second year of growth, but more commonly trees begin flowering in the third year after establishment. Flowers are fully double, light pink, and very attractive. Flowering usually begins in mid March in Raleigh, N.C.; the date of first bloom typically occurs from March 15 to March 30. Full bloom typically occurs from March 25 to April 10, depending on weather conditions. Bloom duration is typically 10–14 days, and individual flowers last about 7–10 days, depending on temperature during bloom. The chilling requirement is estimated to be 950 hours below 4 C, based on comparison of flowering time to peach varieties 'Contender' (unpatented), 'Winblo (unpatented)', and 'Clayton' (unpatented) at the Raleigh, N.C. test location.

Although 'Corinthian Pink' is self fertile and can produce fruit as a result of self pollination, fertility of flowers is poor, for unknown reasons, unrelated to the pollination requirements of the tree, and fruit set is generally low in most years. It is estimated that less than 1% of flowers produced set fruit. Fruit are very small, bitter tasting, and of no horticultural importance in this variety. Fruit ripen in mid to late August in Raleigh, N.C.

The new variety has been named the CORINTHIAN PINK cultivar.

BRIEF DESCRIPTION OF THE DRAWINGS

The accompanying photographs show typical specimens of the entire tree during and after flowering, and close-up pictures of the foliage, flowers, and fruit in color as nearly true as it is reasonably possible to make in a color illustration of this character.

FIGS. 5 and 6 photographed on Aug. 23, 2000.

DETAILED DESCRIPTION OF THE NEW VARIETY

Figure 1:
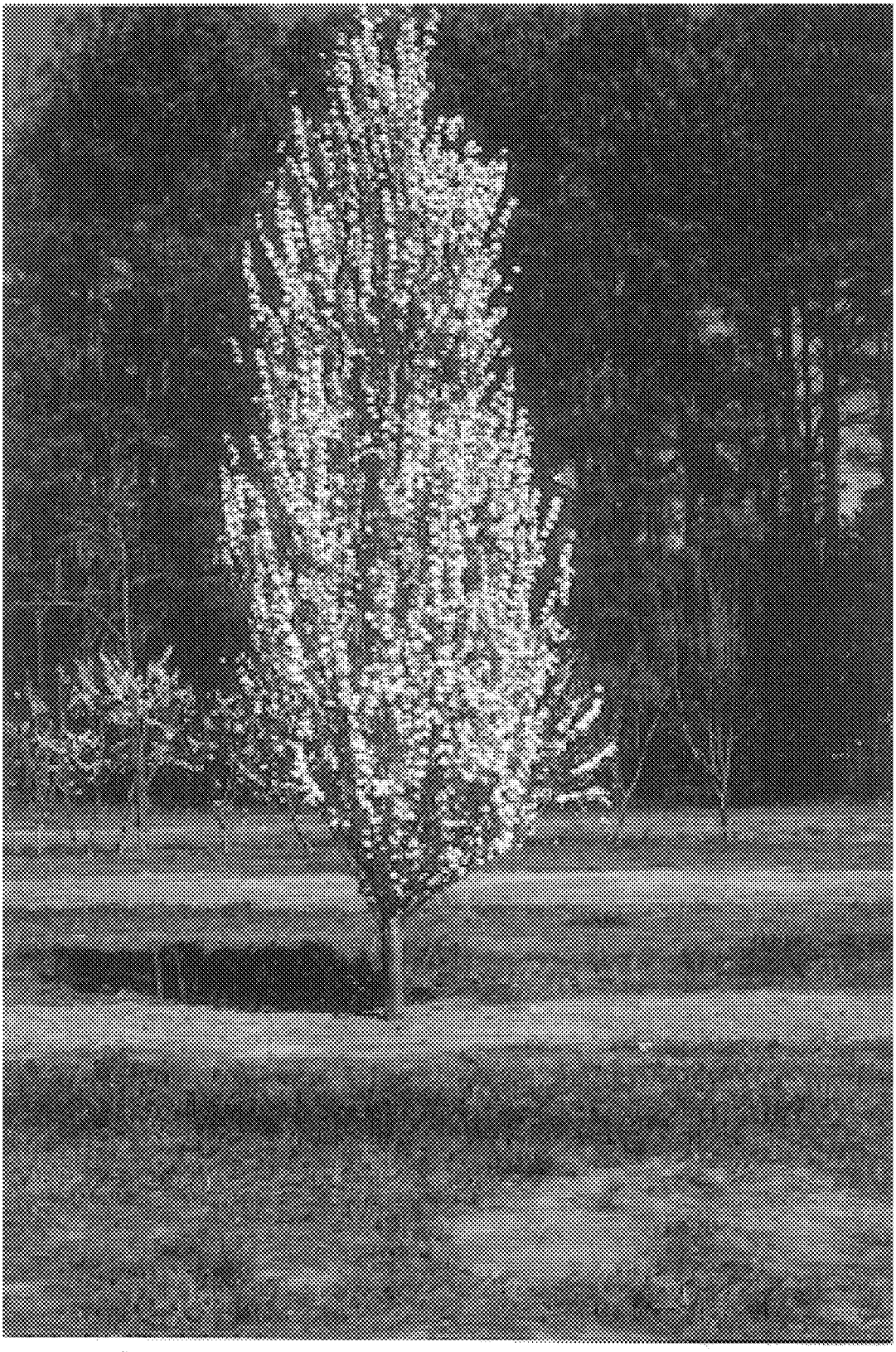
FIG. 1 shows a four-year-old tree of 'Corinthian Pink' in full bloom at Raleigh, N.C., showing the narrowly columnar tree architecture, flower color, and heavy flowering characteristics.
Figure 2:
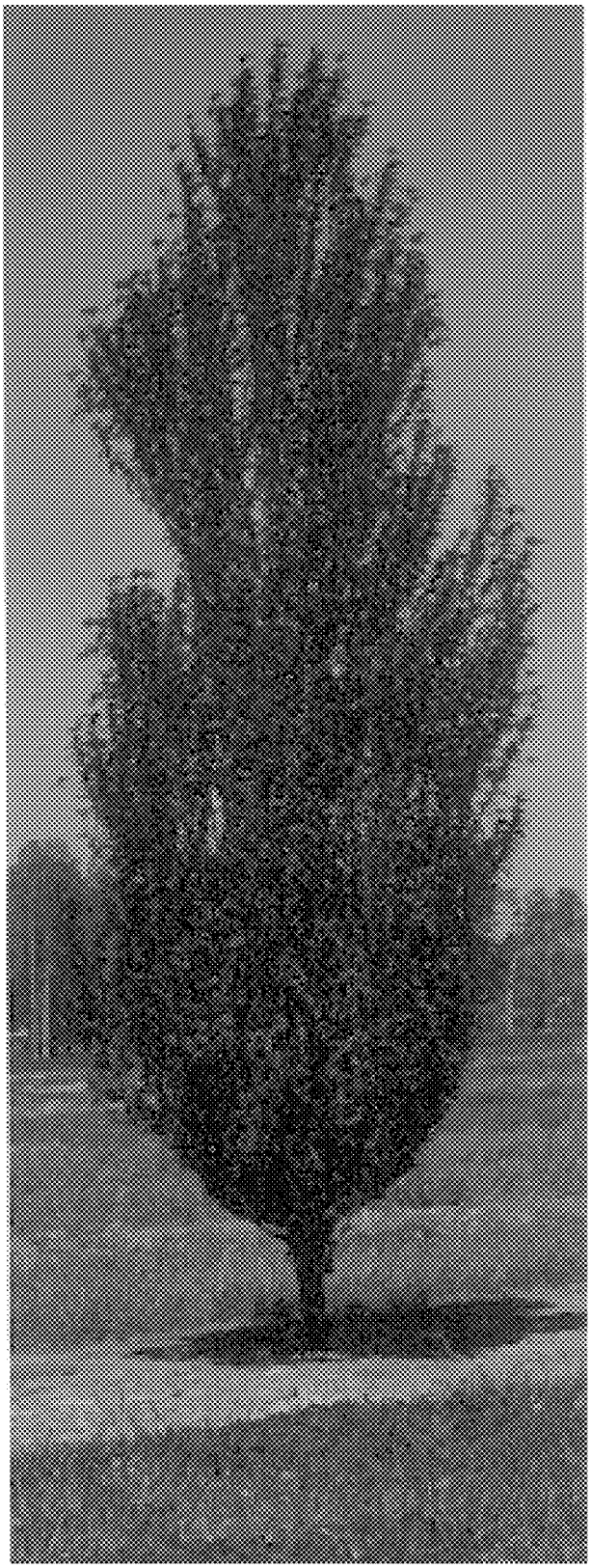
FIG. 2 shows a four-year-old tree of 'Corinthian Pink' taken after flowering, showing the narrowly columnar architecture and theoverall foliage color.
Figure 3:
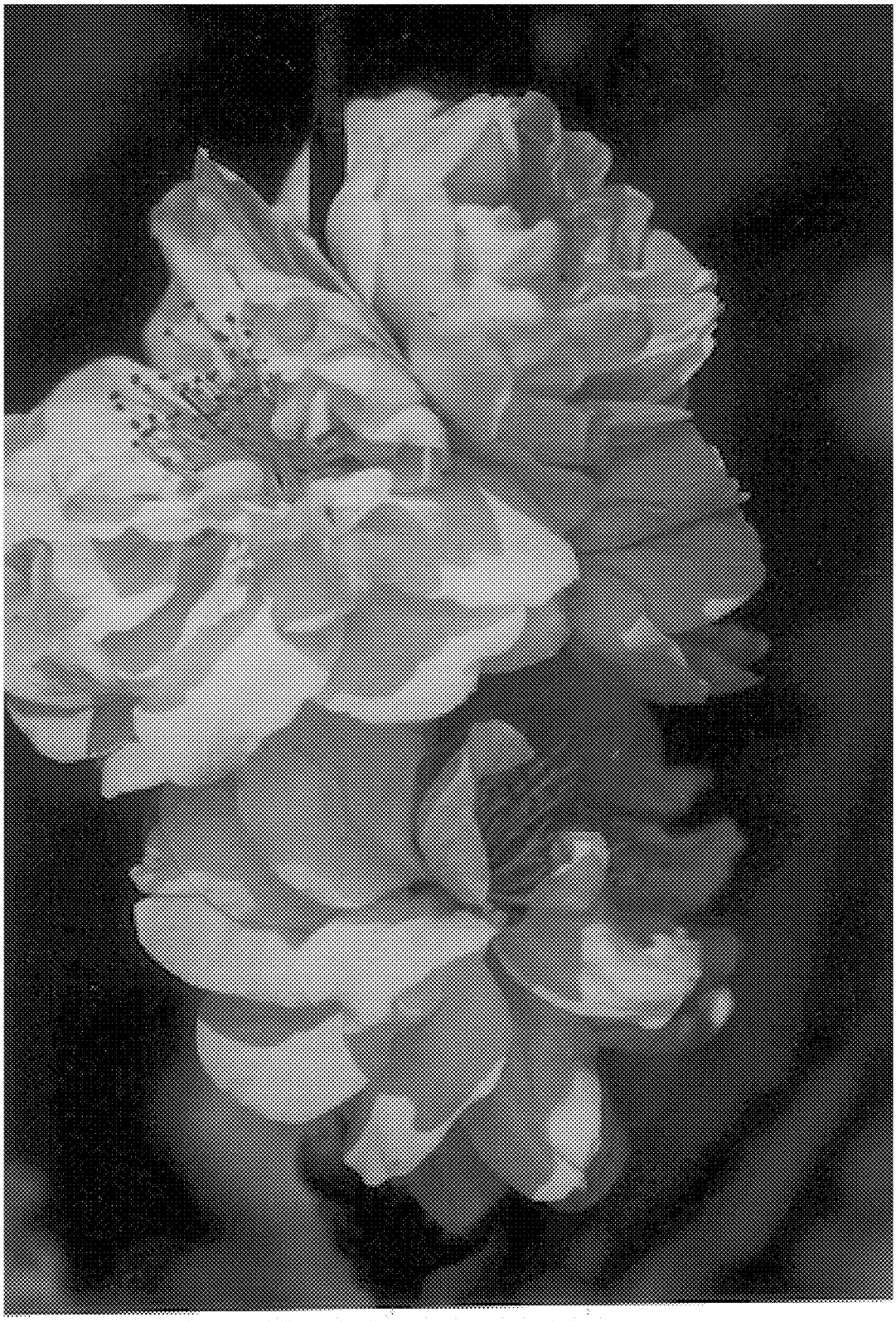
FIG. 3 shows a close up photograph of the flower of 'Corinthian Pink', showing the double flower structure, and the light pink flower color.
Figure 4:
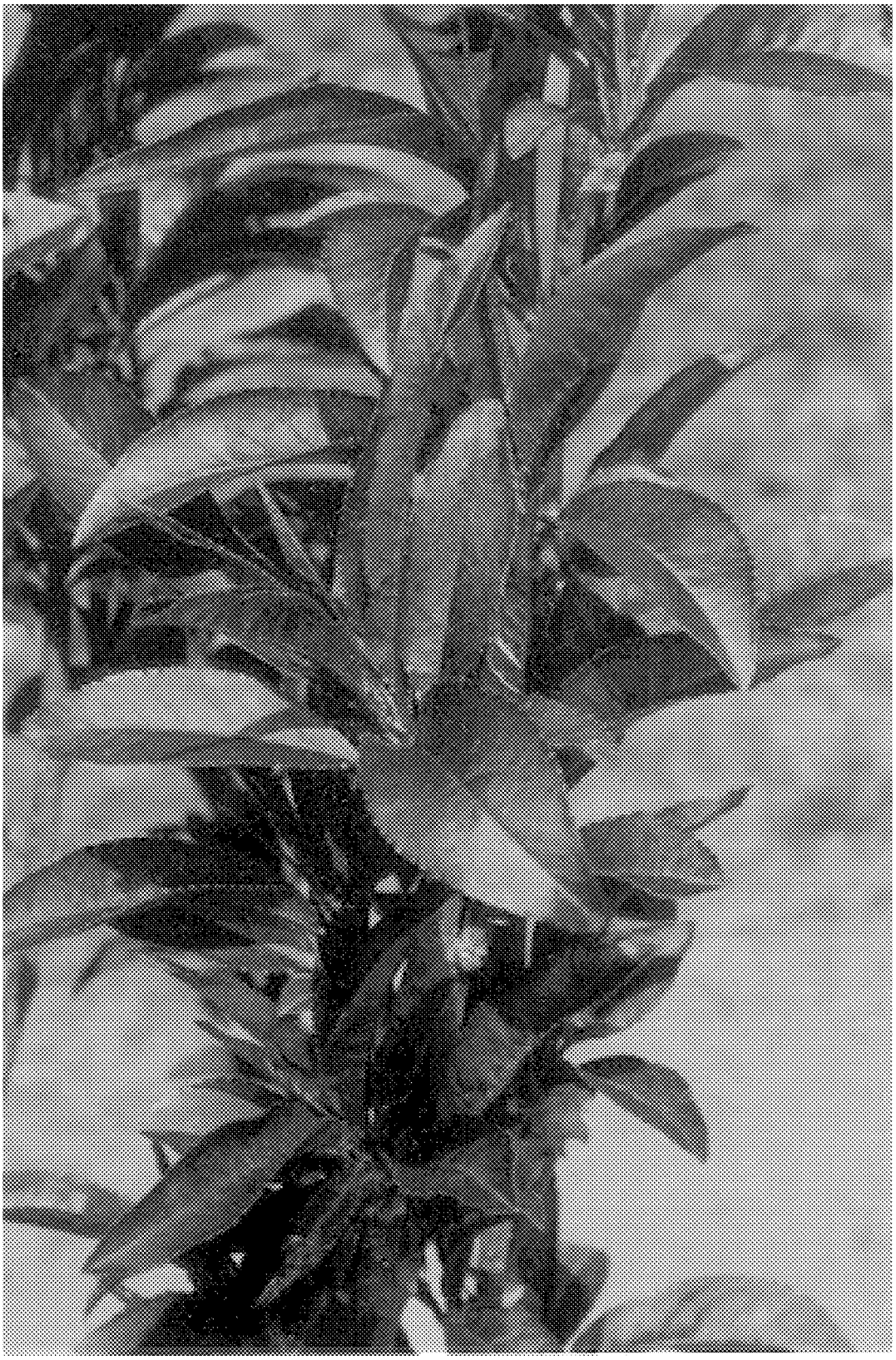
FIG. 4 shows a close-up photograph of the foliage of 'Corinthian Pink' taken about 3 weeks after bud break in the spring.
Figure 5:
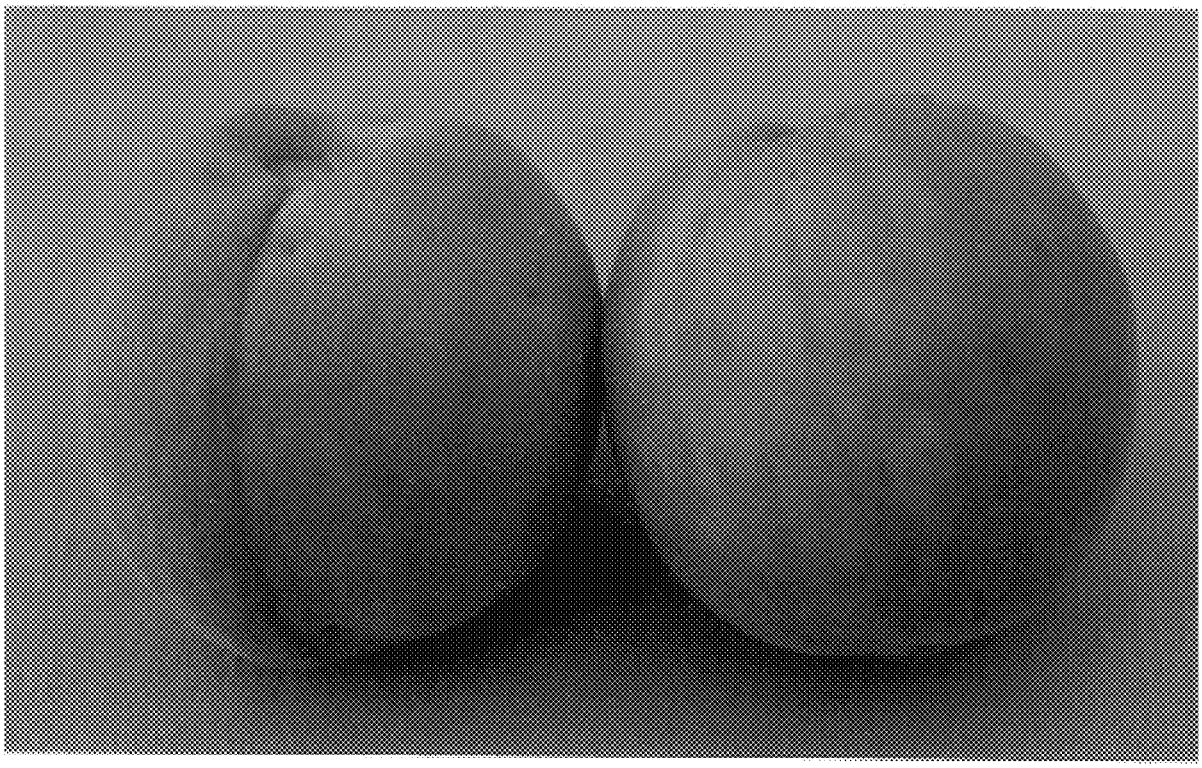
FIG. 5 shows a close-up of the mature fruit of 'Corinthian Pink'.
Figure 6:
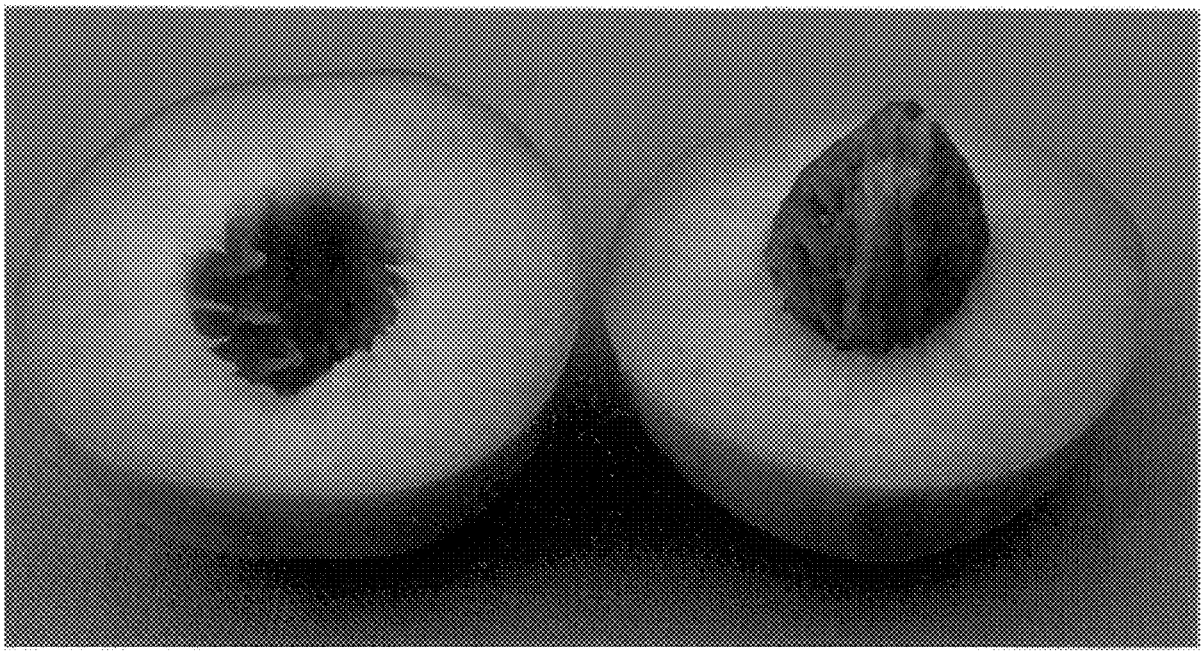
FIG. 6 shows a photograph of the fruit flesh and stone of 'Corinthian Pink'.

The following is a detailed description of the botanical and pomological characteristics of the subject peach. Color data are presented in Royal Horticultural Society Colour chart designations. Where dimensions, sizes, colors and other characteristics are given, it is to be understood that such characteristics are approximations of averages set forth as accurately as practicable.

The descriptions reported herein are from specimens grown at Raleigh, N.C. unless otherwise noted.

Tree:

*Size*.—Large. 14–16 ft. height after four years of growth.

*Vigor*.—Very vigorous.

*Growth*.—Narrowly columnar.

*Fruit production*.—Low.

*Pest resistance*.—Susceptible to peach tree borer, moderately resistant to bacterial leaf spot (Sandhills Research Station observations).

Trunk:

*Size*.—Medium.

*Texture*.—Medium to rough.

*Color*.—Gray-green (197-B).

Branches:

*Size*.—Medium.

*Surface*.—Smooth (new) to medium rough (old).

*Lenticels*.—Medium size. Medium number.

*Color*.—Bright green with slight red blush on sun-exposed portion (new growth). Dormant one-year-old shoots gray-red (178-A). Dormant two-year-old shoots gray-brown (199-A).

Foliage:

*Leaves*.—Large. Mature leaf length 14.1 cm; width 4.8 cm.

*Form*.—Lanceolate. Acutely pointed. Leaf base cuneate.

*Thickness*.—Medium.

*Texture*.—Smooth to slightly rugose.

*Margin*.—Crenate.

*Petiole*.—Medium length (11.9 mm). Color yellow-green (146B).

*Stipules*.—Present. Small.

*Pubescence*.—Absent on both lower and upper surfaces.

*Venation*.—Pinnate. Color or main vein=red (53-A).

*Glands*.—Average number 3. Varies from 2 to 5. Located on base of leaf and upper portion of petiole. Reniform. Color same as upper leaf blade (183-A).

*Color*.—Upper surface —Medium purple 183-A (newly emerged) to grayish red 178-B (mature leaf). Lower surface (newly emerged) 183-B.

*Density*.—Dense.

Flower buds:

*Size*.—Large.

*Length*.—Medium.

*Shape*.—Plump, slightly tapered at apex. Typical of peach.

*Color*.—Light brown.

*Pubescence*.—Lacking.

Flowers:

*Date of first bloom*.—March 15 to March 30. Varies yearly due to weather conditions.

*Date of full bloom*.—March 25 to April 10. Varies yearly due to weather conditions.

*Size*.—Large (diameter=38 mm when fully open), double, showy.

*Petal color*.—Light pink (red 56-D, newly emerged flowers, red 56A, mature flowers).

*Calyx color*.—Grayed-purple (183-A).

*Pedicel*.—Long. Length=14 mm. Color=142-C.

*Reproductive organs*.—Stamens —erect, numerous. Light pink filaments. Pistils—usually one. Pollen —normal and abundant. Bright yellow.

*Number of flowers per bud*.—One.

*Number of petals per flower*.—Average 31.4.

*Fertility*.—Self-fertile, but fruit set low.

Fruit:

*Maturity*.—Late. Mid to late August.

*Size*.—Very small. Average diameter=1.6 in.

*Form*.—Slightly oblong.

*Suture*.—Shallow.

*Pubescence*.—Heavy.

*Skin color*.—Yellowish-green (154-C) with slight red blush (45C), and red streak (45-C) on suture.

*Flesh color*.—Greenish-white (150-D), with small amount of red (46C) near stone.

*Stone*.—Small (average diameter=0.65 in., average weight=3.8 grams). Freestone. Color greyed-orange (172-B).

*Eating quality*.—Very poor.

*Uses*.—None.

The variety: The most distinctive features of the variety are its narrowly columnar growth habit, its medium purple foliage color, and its double (multiple petals) light pink flowers.

We claim:

1. A new and distinct variety of ornamental peach tree, substantially as illustrated and described, characterized by its narrowly columnar growth habit, medium purple foliage color, and large, double, light pink flowers.

* * * * *